United States Patent [19]

Karkhanis

[11] Patent Number: 4,472,302
[45] Date of Patent: Sep. 18, 1984

[54] HEAT SHOCK PROCESS FOR THE ISOLATION OF BACTERIAL PROTEIN

[75] Inventor: Yashwant D. Karkhanis, Fanwood, N.J.

[73] Assignee: Merck & Co., Inc., Rahway, N.J.

[21] Appl. No.: 473,477

[22] Filed: Mar. 9, 1983

[51] Int. Cl.³ .................... C07G 7/00; A61K 39/02; A61K 35/74
[52] U.S. Cl. ................................ 260/112 R; 424/92
[58] Field of Search ...................... 260/112 R; 424/92

[56] References Cited

U.S. PATENT DOCUMENTS 3,718,541  2/1973  Kalina .................... 260/112 R X

OTHER PUBLICATIONS

J. of General Microbiology (1977), 99, 353–357, Morris et al.
Isaacson, *Infection and Immunity*, 15, pp. 272–279, (1977).
DeGraff et al., *Infection and Immunity*, 33, pp. 877–883, (1981).
Altmann et al., *Biochemistry Journal*, 201, pp. 505–513, (1982).
Korhonen et al., *Infection and Immunity*, 27, pp. 569–575, (1980).
Klemm, *European Journal of Biochemistry*, 117, pp. 617–627, (1981).
Evans et al., *Infection and Immunity*, 19, pp. 727–736, (1978).
Fader et al., *The Journal of Biological Chemistry*, 257, pp. 3301–3305, (1982).

*Primary Examiner*—Howard E. Schain
*Attorney, Agent, or Firm*—David L. Rose; Hesna J. Pfeiffer

[57] ABSTRACT

There is disclosed an improved process for the isolation of K-99 outer membrane protein pili from *Escherichia coli* cells. The improved process involves a heat shock treatment of the *E. coli* cells in a buffered solution to afford a release of the K-99 pili into solution which on standing results in the aggregation and precipitation of the pili. The thus isolated K-99 protein pili is useful in the preparation of vaccines.

3 Claims, No Drawings

HEAT SHOCK PROCESS FOR THE ISOLATION OF BACTERIAL PROTEIN

BACKGROUND OF THE INVENTION

The isolation of K-99 outer membrane protein pili from *E. coli* cells is currently practiced using a procedure which involves heating the bacterial cells with urea in a phosphate buffered saline solution. The ultimate isolation of the desired K-99 pili is achieved after a very complex isolation procedure requiring about 10 days' duration. The instant invention describes an improved process for the heating shock treatment of *E. coli* cells and the isolation of the K-99 pili in just a few hours. The isolated pili have uses in the manufacture of vaccines.

SUMMARY OF THE INVENTION

The instant invention is concerned with an improved process for the isolation of K-99 outer membrane protein pili from *E. coli* cells. Specifically, it is concerned with an improved heat shock process to effect such isolation. Thus, it is an object of the invention to describe such heat shock process. It is a further object of this invention to describe the conditions under which the process is carried out and the K-99 pili isolated. Further objects will become apparent from a reading of the following description.

DESCRIPTION OF THE INVENTION

Bacterial pili or fimbriae are filamentous appendages on the surface of the bacteria. They are polymeric but their subunit pilin is of low molecular weight and is predominantly protein in nature. One stricking property shown by all pili proteins is their richness of the content of hydrophobic amino acids. Studies on pili over the past few years have shown that they are adhesion factors which play important roles in the colonization of the bacteria to the host tissue. By anchoring to the receptor on the host cell, the bacteria overcome peristaltic pressure and compete with commensal bacteria for colonization.

Isolation of pure pili is essential to the study of structure function relationships of this protein. Several procedures are now available to obtain pili in purified form. Many of the procedures are long and do not lead to the isolation of homogenous material. Recently investigators have reported procedures which involve the use of urea and sodium deoxycholate in the isolation of pili. These steps facilitated the separation of the pili from membrane components which are associated with pili. In the present invention is presented data on the isolation of pili protein using a new single step procedure.

The improved single step procedure involves the heat shock treatment of the *E. coli* bacteria in a phosphate buffered saline solution. Unlike the prior art procedures, urea is not present in the buffer solution. Thus, where the prior art procedures result in a solution which is difficult to remove the pili from, the present invention affords a solution which, with incubation under the conditions described below, results in such solution becoming turbid due to the aggregation of the pili. The turbid mixture can then be centrifuged and the residue affords the pili directly and in very pure form.

The specific steps involved in the isolation of the pili from the bacteria are the heating of the *E. coli* bacteria cells in a phosphate buffered saline solution at from 55°–65° C. for from 10 to 30 minutes. Generally heating at about 60° C. for about 20 minutes is suitable. Then the heat shock material may be incubated in a supernatant liquid at about 4° C. for from 15 to 20 hours. The heat shock material is then centrifuged to deposit the pili. The centrifugation is carried out at from 30,000 to 50,000 xg for from 30 to 60 minutes. Generally centrifugation at about 40,000 xg for about 20 minutes is sufficient. The centrifuged pellet consists of pure K-99 pili which can be used without further purification. The instant procedure has the added advantage that the yield of the K-99 pili in increased over that obtained by the prior art processes, and is in fact about 4 times greater.

The *E. coli* bacteria that can be used in the instant procedure are those that contain the K-99 pili and generally are those that are enteropathogenic in pigs, calves and lambs causing gastrointestinal symptoms. The *E. coli* strains described in the instant examples are strains from the culture collection of Merck & Co., Inc. which have also been permanently, irrevocably deposited, without restriction, as to availability, in the culture collection of the American Type Culture Collection 12301 Parklawn Drive, Rockville, Md., 20852.

| *E. coli* strain | Merck Culture Collection Number | ATCC Accession Number |
|---|---|---|
| B-41 | MB-3760 | 39303 |
| B-44 | MB-3857 | 39074 |
| 1439 | MB-3712 | 39302 |

The isolated outer membrane protein pili is used for the preparation of vaccines against the gastrointestinal disorders that are caused by the above enteropathogenic bacteria. The efficient preparation of such K-99 protein pili as is afforded by this invention will enhance the preparation of such vaccines.

The following example is being presented in order that the invention might be more fully understood. It is not to be considered as limitative of the invention.

EXAMPLE

K-99 Antigen was isolated from the bovine enterotoxigenic *Escherichia coli* strain B-44 (0.9:K-30:K-99:H−). Minca broth medium as described by Guinee et al. (Infect. Immun. 13, 1369–1377 (1976)) was used to grow the cells. A single colony of B44 was inoculated into a flask containing 100 ml of minca broth and grown overnight with aeration at 37° C. This seed culture was used to inoculate 9 liters of minca broth prewarmed to 37° C. in a 12 liter fermentor. The culture was incubated for 24 hours with vigorous stirring and aeration and harvested by centrifugation in a Dupont-Sorvall 5B superspeed centrifuge at 4° C. in a GS-3 head at 10,000 xg. The packed cells were resuspended in approximately 100 ml of sterile phosphate buffered saline and divided into four 25 ml aliquots and 35 ml polycarbonate centrifuge tubes. These aliquots were subjected to a heat shock at 65° C. for 20 minutes with occasional mixing to ensure even heating. The tubes were centrifuged at 24,500 xg for 20 minutes and the supernatant retained for pilus isolation.

The heat shock material was kept at 4° C. for 16 hours. The turbid solution was centrifuged at 39,100 xg for 20 minutes; the supernatant was saved and, since some pili are present, can be processed using prior art techniques to remove such pili. The pellet was suspended in 100 ml, 50 mM phosphate buffer and was centrifuged again. This supernatant was discarded. The pellet which consisted of pure K-99 pili was suspended in phosphate buffer at a concentration of 2.5 to 4 mg/ml and retained for characterization for other uses.

The K-99 pili were also isolated from two other strains of *E. coli*, B-41 and 1439, following the same procedure discussed above. The heat shock materials from these strains were incubated at 4° C. for 16 hours and centrifuged to obtain the K-99 pili.

Other K-99 producing strains of *E. coli* are available and described in the prior art and may be used in this procedure. In deGraff et al. in *Inf. and Imm.* 33 877–883 (1980) is described *E. coli* strains F-57 and 1474. In Altmann et al. in *Biochem J.* 201 505–513 (1982) is described *E. coli* strain C-1443 as well as the above described B-41 strain. In Korhonen et al. in *Inf. and Imm.* 27 569–575 (1980) is described *E. coli* strains 3048 and 6013. In Isaacson *Inf. and Imm.* 15 272–279 (1977) is described *E. coli* strains 1474 and 1475 as well as the above described B-41 strain.

What is claimed is:

1. A process for the isolation of K-99 outer membrane protein pili from *E. Coli* bacteria cells which consists of the heat shock treatment of cells of the strains B-41 (MB-3760, ATCC 37303); B-44 (MB-3857, ATCC 39074); or 1439 (MB-3712, ATCC 39302) at from 50° to 65° C. for from 10 to 30 minutes in a phosphate buffer saline solution; incubation of the heat shocked material at about 4° C. for from 15 to 20 hours; and the centrifugation of the incubated heat shock material to recover the precipitated pili.

2. The process of claim 1 wherein the heating is carried out at about 60° C. for about 20 minutes.

3. The process of claim 1 wherein the heat shock material is incubated at about 4° C. for about 16 hours prior to centrifugation.

* * * * *